United States Patent
Pelton et al.

(10) Patent No.: US 7,658,760 B2
(45) Date of Patent: *Feb. 9, 2010

(54) THERMOELASTIC AND SUPERELASTIC NI-TI-W ALLOY

(75) Inventors: Brian Lee Pelton, Menlo Park, CA (US); John F. Boylan, Murrieta, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/917,701

(22) Filed: Aug. 13, 2004

(65) Prior Publication Data

US 2005/0021129 A1    Jan. 27, 2005

Related U.S. Application Data

(63) Continuation of application No. 10/406,999, filed on Apr. 3, 2003, now Pat. No. 6,776,795, which is a continuation of application No. 09/752,785, filed on Dec. 28, 2000, now Pat. No. 6,569,194.

(51) Int. Cl.
*A61F 2/06*     (2006.01)
*A61F 2/82*     (2006.01)
(52) U.S. Cl. .................................... 623/1.19; 623/1.34
(58) Field of Classification Search ................ 623/1.15, 623/1.19, 1.34
See application file for complete search history.

(56) References Cited

U.S. PATENT DOCUMENTS

| | | | |
|---|---|---|---|
| 3,063,835 A | 11/1962 | Stern | |
| 4,503,569 A | 3/1985 | Dotter | |
| 4,538,622 A | 9/1985 | Samson et al. | |
| 4,580,568 A | 4/1986 | Gianturco | |
| 4,665,906 A | 5/1987 | Jervis | |
| 4,856,516 A | 8/1989 | Hillstead | |
| 4,934,380 A | 6/1990 | de Toledo | |
| 4,966,163 A | 10/1990 | Kraus et al. | |
| 5,067,957 A | 11/1991 | Jervis | |
| 5,092,877 A | 3/1992 | Pinchuk | |

(Continued)

FOREIGN PATENT DOCUMENTS

EP     0 873734 A2     10/1998

(Continued)

OTHER PUBLICATIONS

Schetky, L. McDonald, Shape Memory Alloys, *Scientific American*, 281,74-82 (Nov. 1979).

(Continued)

*Primary Examiner*—Thomas J Sweet
(74) *Attorney, Agent, or Firm*—Workman Nydegger

(57) ABSTRACT

A radiopaque nitinol stent for implantation in a body lumen is disclosed. The stent is made from a superelastic alloy such as nickel-titanium or nitinol, and includes a ternary element including tungsten. The added tungsten in specified amounts improve the radiopacity of the nitinol stent comparable to that of a stainless steel stent of the same strut pattern coated with a thin layer of gold. Furthermore, the nitinol stent has improved radiopacity yet retains its superelastic and shape memory behavior and further maintains a thin strut/wall thickness for high flexibility.

19 Claims, 2 Drawing Sheets

U.S. PATENT DOCUMENTS

| | | | |
|---|---|---|---|
| 5,190,546 A | 3/1993 | Jervis | |
| 5,201,901 A | 4/1993 | Harada et al. | |
| 5,292,331 A | 3/1994 | Boneau | |
| 5,350,419 A | 9/1994 | Bendel et al. | |
| 5,356,418 A | 10/1994 | Shturman | |
| 5,411,476 A | 5/1995 | Abrams et al. | |
| 5,514,154 A | 5/1996 | Lau et al. | |
| 5,562,641 A | 10/1996 | Flomenblit et al. | |
| 5,569,295 A | 10/1996 | Lam | |
| 5,597,378 A | 1/1997 | Jervis | |
| 5,628,787 A | 5/1997 | Mayer | |
| 5,637,089 A | 6/1997 | Abrams et al. | |
| 5,641,364 A | 6/1997 | Golberg et al. | |
| 5,667,522 A | 9/1997 | Flomenblit et al. | |
| 5,690,644 A | 11/1997 | Yurek et al. | |
| 5,725,570 A | 3/1998 | Heath | |
| 5,725,572 A | 3/1998 | Lam et al. | |
| 5,741,327 A | 4/1998 | Frantzen | |
| 5,800,526 A | 9/1998 | Anderson et al. | |
| 5,843,244 A | 12/1998 | Pelton et al. | |
| 5,885,381 A | 3/1999 | Mitose et al. | |
| 5,902,317 A | 5/1999 | Kleshinski et al. | |
| 5,907,893 A | 6/1999 | Zadno-Azizi et al. | |
| 5,927,345 A | 7/1999 | Samson | |
| 5,931,819 A | 8/1999 | Fariabi | |
| 5,948,016 A | 9/1999 | Jang | |
| 5,951,793 A | 9/1999 | Mitose et al. | |
| 5,954,724 A | 9/1999 | Davidson | |
| 5,954,744 A | 9/1999 | Phan et al. | |
| 5,980,531 A | 11/1999 | Goodin et al. | |
| 6,017,362 A | 1/2000 | Lau | |
| 6,022,374 A | 2/2000 | Imran | |
| 6,059,810 A | 5/2000 | Brown et al. | |
| 6,077,295 A | 6/2000 | Limon et al. | |
| 6,086,610 A | 7/2000 | Duerig et al. | |
| 6,132,389 A | 10/2000 | Cornish et al. | |
| 6,137,060 A | 10/2000 | Avellanet | |
| 6,174,329 B1 | 1/2001 | Callol et al. | |
| 6,183,409 B1 | 2/2001 | Armini | |
| 6,241,762 B1 * | 6/2001 | Shanley | 623/1.17 |
| 6,278,057 B1 | 8/2001 | Avellanet | |
| 6,312,455 B2 * | 11/2001 | Duerig et al. | 623/1.19 |
| 6,325,824 B2 | 12/2001 | Limon | |
| 6,334,871 B1 | 1/2002 | Dor et al. | |
| 6,344,041 B1 | 2/2002 | Kupiecki et al. | |
| 6,364,902 B1 | 4/2002 | Dickenson et al. | |
| 6,380,457 B1 | 4/2002 | Yurek et al. | |
| 6,387,060 B1 | 5/2002 | Jalisi | |
| 6,387,123 B1 | 5/2002 | Jacobs et al. | |
| 6,569,194 B1 * | 5/2003 | Pelton | 623/1.15 |
| 6,572,646 B1 * | 6/2003 | Boylan et al. | 623/1.12 |
| 6,620,192 B1 | 9/2003 | Jalisi | |
| 6,638,301 B1 | 10/2003 | Chandrasekaran et al. | |
| 6,755,855 B2 | 6/2004 | Yurek et al. | |
| 6,776,795 B2 * | 8/2004 | Pelton | 623/1.19 |
| 6,855,161 B2 * | 2/2005 | Boylan et al. | 623/1.19 |
| 7,128,757 B2 | 10/2006 | Boylan et al. | |
| 2001/0001317 A1 | 5/2001 | Duerig et al. | |
| 2001/0049549 A1 | 12/2001 | Boylan et al. | |
| 2002/0052627 A1 | 5/2002 | Boylan et al. | |
| 2002/0082681 A1 | 6/2002 | Boylan et al. | |
| 2002/0138133 A1 | 9/2002 | Lenz et al. | |
| 2003/0018381 A1 | 1/2003 | Whitcher et al. | |
| 2003/0050684 A1 | 3/2003 | Abrams et al. | |
| 2003/0121148 A1 | 7/2003 | DiCaprio | |
| 2003/0191520 A1 | 10/2003 | Pelton | |
| 2003/0203991 A1 | 10/2003 | Schottman et al. | |
| 2003/0216668 A1 | 11/2003 | Howland et al. | |
| 2004/0092818 A1 | 5/2004 | Weaver et al. | |
| 2004/0143320 A1 | 7/2004 | Calisse | |
| 2004/0148015 A1 | 7/2004 | Lye et al. | |
| 2004/0167496 A1 | 8/2004 | Poole et al. | |
| 2004/0193257 A1 | 9/2004 | Wu et al. | |
| 2004/0220608 A1 | 11/2004 | D'Aquanni et al. | |
| 2005/0060025 A1 | 3/2005 | Mackiewicz et al. | |
| 2005/0171600 A1 | 8/2005 | Harnek et al. | |
| 2005/0244459 A1 | 11/2005 | DeWitt et al. | |
| 2006/0015170 A1 | 1/2006 | Jones et al. | |
| 2006/0115514 A1 | 6/2006 | Gengrinovitch | |
| 2006/0122694 A1 | 6/2006 | Stinson et al. | |
| 2006/0129166 A1 | 6/2006 | Lavelle | |
| 2006/0190070 A1 | 8/2006 | Dieck et al. | |
| 2007/0050017 A1 | 3/2007 | Sims et al. | |
| 2007/0100431 A1 | 5/2007 | Bonsignore et al. | |
| 2007/0135891 A1 | 6/2007 | Schneider | |
| 2007/0184083 A1 | 8/2007 | Coughlin | |
| 2007/0191812 A1 | 8/2007 | Nishide et al. | |
| 2007/0202351 A1 | 8/2007 | Justin et al. | |
| 2007/0239205 A1 | 10/2007 | Yang et al. | |
| 2007/0244548 A1 | 10/2007 | Myers et al. | |
| 2007/0250158 A1 | 10/2007 | Krivoruchko et al. | |
| 2007/0280850 A1 | 12/2007 | Carlson | |
| 2008/0033531 A1 | 2/2008 | Barthel et al. | |
| 2008/0053577 A1 | 3/2008 | Syed et al. | |
| 2008/0071347 A1 | 3/2008 | Cambronne | |
| 2008/0091267 A1 | 4/2008 | Stinson et al. | |
| 2008/0178459 A1 | 7/2008 | Barr et al. | |
| 2008/0195194 A1 | 8/2008 | Pacetti et al. | |
| 2008/0288056 A1 | 11/2008 | Simpson et al. | |

FOREIGN PATENT DOCUMENTS

| | | |
|---|---|---|
| EP | 1 479 358 | 11/2004 |
| GB | 2 156 850 | 10/1985 |
| JP | 62060836 | 3/1987 |
| JP | 62211334 | 9/1987 |
| JP | 62235449 | 10/1987 |
| JP | 3253529 | 11/1991 |
| JP | 7197221 | 8/1995 |
| JP | 11036024 | 2/1999 |
| JP | 2002212664 | 7/2002 |
| WO | WO 02/36045 | 5/2002 |
| WO | WO 02/064019 | 8/2002 |
| WO | WO 03/026715 | 4/2003 |
| WO | WO 2004/033016 | 4/2004 |
| WO | WO 2005/049876 | 6/2005 |
| WO | WO 2006/048853 | 5/2006 |
| WO | WO 2006/081011 | 8/2006 |
| WO | WO 2007/019478 | 2/2007 |
| WO | WO 2008/125153 | 10/2008 |
| WO | WO 2008/137547 | 11/2008 |
| WO | WO 2009/014696 | 1/2009 |

OTHER PUBLICATIONS

Duerig, T. W. et al., An Engineer's Perspective of Pseudoelasticity, *Engineering Aspects of Shape Memory Alloys*, pp. 369-393 (1990).

Enami, K. et al., Effect of W Addition on the Martensitic Transformation and Shape Memory Behavior of The Ti Ni- Base Alloys, *Journal De Physique IV*, 5, C8, 629-C86, (Dec. 1995).

Russell, S. M. et al., Improved Ni Ti Alloys for Medical Applications, *Proceeidngs of the Second International Conference on Shape Memory and Superelastic Technologies*, 429-436 (1997).

U.S. Appl. No. 09/452,516 (Boylan) titled itinol Alloy Design and Composition for Vascular Stents, filed Dec. 1, 1999.

Anomet Products—Medical Devices, Source: http://anometproducts.com/products_medical.html.

Bender, Matthew D., Computational Design and Precipitation-Strengthened Titanium-Nickel-Based Shape Memory Alloys, Ph. D. Dissertation, Northwestern University, 2008 212 pages; AAT 3331081.

Duerig, Tom, Nitionol: The Shape of Things to Come, Mar. 1, 2006, Source: http://www.medicaldevice-network.com/features/feature116/.

Eckelmeyer, K.H., The Effect of Alloying on the Shape Memory Phenomenon in Nitinol, Scripta Metallurgica, vol. 10, No. 8, p. 667-672, Aug. 1976.

Ellner, M., Bond Energy in Palladium and Platinum-Rich Alloys With The A/sup 4/transition Metals, Journal of Alloys and Compounds, vol. 366, p. 222-7.

Khachin, V.N., Martensitic Inelasticity of Alloys, Russian Physics Journal, vol. 28, No. 5, May 1985, pp. 404-415; ISSN 1064-8887 (Print) 1573-9228 (online) DOI 10.1007/BF00892273.

Lin Brian, Graduate Student Research Objective, Source: http://www.advancedmaterialslab.com/people/graduates/brian/.

Lin, Brian; Ken Gall, Hans J. Maier, Robbie Waldron; Structure and thermomechanical behavior of NiTiPt shape memory alloy wires; Acta Biomaterialia, vol. 5, Issue 1, Jan. 2009, pp. 257-267.

Lindquist, Paul George, "Structure and transformation behavior of martensitic titanium-(nickel, palladium) and titainium-(nickel, platinum) alloys", Ph. D. Dissertation, University of Illinois at Urbana-Champaign, 1988, 131 pages; AAT 8908756.

Lindquist, P.G. and C.M. Wayman, Shape Memory and Transformation Behavior of Martensitic Ti-Pd-Ni and Ti-Pt-Ni Alloys, Engineering Aspects of Shape Memory Alloys, pp. 58-68.

Noebe, R.D., Draper, S.L. Biles, T.A. Leonhardt, T., Processing of Ni30Pt20Ti50 High-Temperature Shape-Memory Alloy Into Thin Rod Demonstrated, NASA Glenn Research Center, Jun. 2005.

Noolu, N. J., Kerr, H.W., Zhou, Y., Xie, J., Laser Weldability of Pt and Ti Alloys, Materials Science and Engineering A., vol. 397, Issues 1-2, Apr. 24, 2005, pp. 8-15.

Okazaki, Y.; Ito, A.; Tateishi, T., Ito, Y., Effect of Alloying Elements On Anodic Polarization Properties of Titanium Alloys in Acid Solutions, Materials Transactions, JIM vol. 35, No. 1, pp. 58-66, Jan. 1994.

SAES Smart Materials, Heat Treating and Shape Setting, Source: http://www.shape-memory-alloys.com/heat_treating_shapesetting.html.

Schaffer, Jermey E., Richard Gordon, "Engineering Characteristics of Dawn Filled Nitinol Tube", Source: http://www.fortwaynemetals.com/resources_witepapers/NitiDFT.pdf.

Soboyejo, W.O., Srivatsan, T.S., Advanced Structural Materials (Book), CRC Press, 2007, ISBN 1574446347, 9781574446340 (Summary and Excerpt).

U.S. Appl. No. 09/752,785, Apr. 9, 2002, Office Action.
U.S. Appl. No. 09/752,785, Nov. 4, 2002, Office Action.
U.S. Appl. No. 09/752,785, May 8, 2003, Issue Notification.
U.S. Appl. No. 10/406,999, Dec. 23, 2003, Office Action.
U.S. Appl. No. 10/406,999, Apr. 6, 2004, Notice of Allowance.
U.S. Appl. No. 10/406,999, Jul. 29, 2004, Issue Notification.

Bigelow, Glen, et al., Development and Characterization of Improved High Temperature Shape Memory Alloys by Solid Solution Strengthening of Ternary NiTiPd Alloys, Materials and Structures Division, NASA Glenn Research Center, The International Conference on Shape Memory and Superelastic Technologies 2006, pp. 113-131.

Boriskina, N. G., et al., Phase Euilibria and Some Properties of Alloys of the Ti-TiPd-TiNi System at 400 degrees C, Izvestiya Akademii Nauk SSSR, Metally No. 5, pp. 6-9, 1982.

Brown, Stanley A., Lemons, Jack E., Medical Applications of Titanium and Its Alloy, Proceedings of a symposium held in 1994 on Phoenix, Arizona, Published by ASTM International, 1996, ISBN 0803120109, 9780803120105 (Overview).

Lin, Z.C., Corrosion Study of NiTiPt and NitiPt Marker Stents, Proceedings of the International Conference of Shape Memory and Superelastic Technologies, Oct. 3-7, 2004, ISBN 0871708345, 9780871708342, pp. 375-380.

* cited by examiner

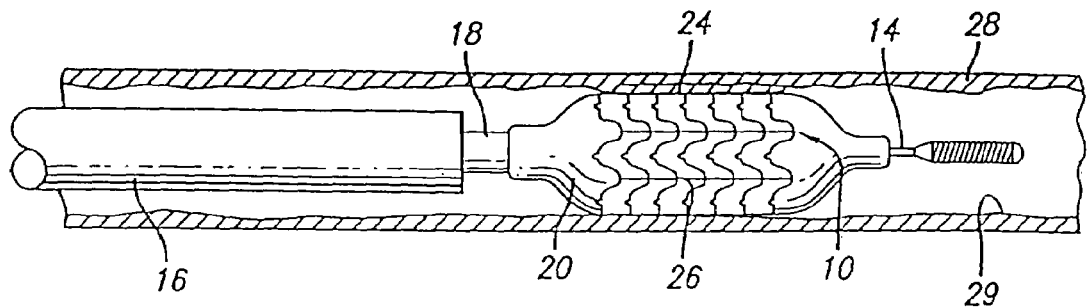
FIG. 1
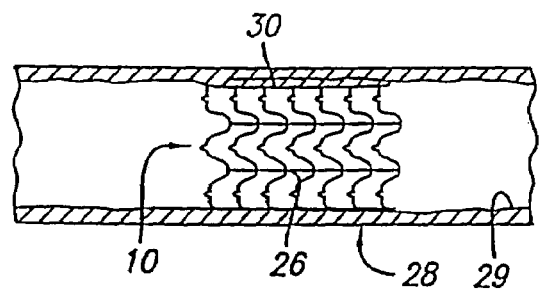
FIG. 2
FIG. 3
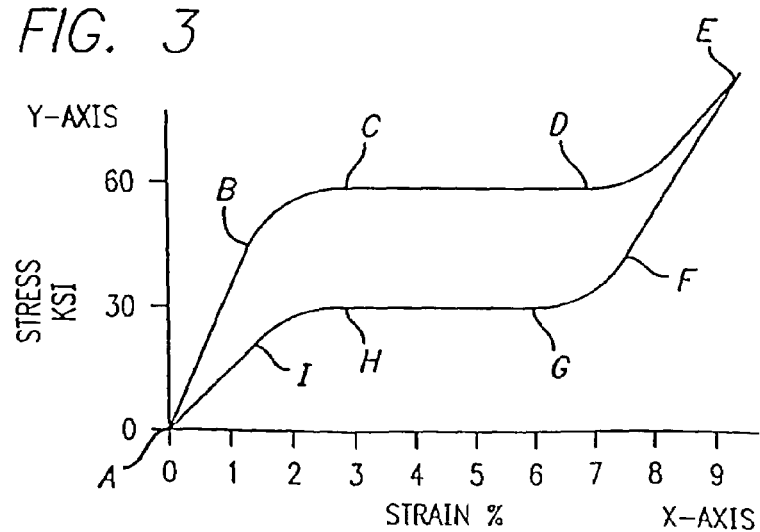

THERMOELASTIC AND SUPERELASTIC NI-TI-W ALLOY

CROSS-REFERENCE TO RELATED APPLICATIONS

This is a continuation application of a application having U.S. Ser. No. 10/406,999 filed Apr. 3, 2003, now U.S. Pat. No. 6,776,795, and which is a continuation of U.S. Ser. No. 09/752,785 filed Dec. 28, 2000, now U.S. Pat. No. 6,569,194 B1, the contents of all of which are hereby incorporated by reference.

BACKGROUND OF THE INVENTION

The present invention generally relates to self-expanding endoprosthetic devices including self-expanding intraluminal vascular grafts, generally called stents. More precisely, the present invention relates to stents made of radiopaque nitinol that can be used in essentially any body lumen.

Stents are typically implanted in a body lumen, such as carotid arteries, coronary arteries, peripheral arteries, veins, or other vessels to maintain the patency of the lumen. These devices are frequently used in the treatment of atherosclerotic stenosis in blood vessels especially after percutaneous transluminal angioplasty (PTA) or percutaneous transluminal coronary angioplasty (PTCA) procedures with the intent to reduce the likelihood of restenosis of a vessel. Stents are also used to support a body lumen, tack-up a flap or dissection in a vessel, or in general where the lumen is weak to add support.

During PTCA procedures it is common to use a dilation catheter to expand a diseased area to open the patient's lumen so that blood flows freely. Despite the beneficial aspects of PTCA procedures and its widespread and accepted use, it has several drawbacks, including the possible development of restenosis and perhaps acute thrombosis and sub-acute closure. This recurrent stenosis has been estimated to occur in seventeen to fifty percent of patients despite the initial PTCA procedure being successful. Restenosis is a complex and not fully understood biological response to injury of a vessel which results in chronic hyperplasia of the neointima. This neointimal hyperplasia is activated by growth factors which are released in response to injury. Acute thrombosis is also a result of vascular injury and requires systemic antithrombotic drugs and possibly thrombolytics as well. This therapy can increase bleeding complications at the catheter insertion site and may result in a longer hospital stay. Sub-acute closure is a result of thrombosis, elastic recoil, and/or vessel dissection.

Several procedures have been developed to combat restenosis and sub-acute or abrupt closure, one of which is the delivery and implanting of an intravascular stent. Stents are widely used throughout the United States and in Europe and other countries. Generally speaking, the stents can take numerous forms. One of the most common is a generally cylindrical, hollow tube that holds open the vascular wall at the area that has been dilated by a dilation catheter. One highly regarded stent used and sold in the United States is known under the tradename ACS Multi-Link Stent, which is made by Advanced Cardiovascular Systems, Inc., Santa Clara, Calif.

In expandable stents that are delivered with expandable catheters, such as balloon catheters, the stents are positioned over the balloon portion of the catheter and are expanded from a reduced diameter to an enlarged diameter greater than or equal to the inner diameter of the arterial wall by inflating the balloon. Stents of this type can be expanded to an enlarged diameter by deforming the stent, by engagement of the stent walls with respect to one another, and by one way engagement of the stent walls together with endothelial growth onto and over the stent.

Examples of intravascular stents can be found in U.S. Pat. No. 5,292,331 (Boneau); U.S. Pat. No. 4,580,568 (Gianturco); U.S. Pat. No. 4,856,516 (Hillstead); U.S. Pat. No. 5,092,877 (Pinchuk); and U.S. Pat. No. 5,514,154 (Lau et al.), which are incorporated herein by reference in their entirety.

The problem with some prior art stents, especially those of the balloon expandable type, is that they are often stiff and inflexible. These balloon expandable type stents are commonly formed from stainless steel alloys and the stents are constructed so that they are expanded beyond their elastic limit. As a result, such stents are permanently deformed by the inflation balloon beyond their elastic limits to hold open a body lumen and thus maintain patency of that body lumen. There are several commercially available balloon expandable stents that are widely used; they are generally implanted in the coronary arteries after a PTCA procedure mentioned earlier.

Stents are often times implanted in vessels that are closer to the surface of the body, such as in the carotid arteries in the neck or in peripheral arteries and veins in the leg. Because these stents are so close to the surface of the body, they are particularly vulnerable to impact forces that can partially or completely collapse the stent and thereby block fluid flow in the vessel. Other forces can impact balloon expandable stents and cause similar partial or total vessel blockage. For instance, under certain conditions, muscle contractions might also cause expandable stents to collapse partially or completely. The collapse occludes the lumen and restricts blood flow in the vessel in which they are implanted.

Since balloon expandable stents are plastically deformed, once collapsed or crushed they remain so, permanently blocking the vessel. Thus, balloon expandable stents under certain conditions might pose an undesirable condition for the patient.

Self-expanding stents as the name implies self-expand through the properties of the material constituting the stent. The inflation force of a balloon catheter is usually not necessary to deploy this kind of stent.

Important applications including those mentioned above have prompted designers to seek out superelastic shape memory alloys to exploit the materials' properties in their self-expanding stents. Examples of applying superelastic nickel-titanium alloys to a self-expanding stent and other medical devices are disclosed in U.S. Pat. Nos. 4,665,906; 5,067,957; 5,190,546; and 5,597,378 to Jervis and U.S. Pat. No. 4,503,569 to Dotter. Another example is disclosed in European Patent Application Publication No. EP0873734A2, entitled "Shape Memory Alloy Stent." This publication suggests a stent for use in a lumen in a human or animal body having a generally tubular body formed from a shape memory alloy which has been treated so that it exhibits enhanced elastic properties. The publication further suggests use of specified ternary elements in a nickel-titanium alloy to obtain desired engineering characteristics.

Use of a ternary element in a superelastic stent is also shown in, for example, U.S. Pat. No. 5,907,893 to Zadno-Azizi et al. As a general proposition, there have been attempts at adding a ternary element to nickel-titanium alloys as disclosed in, for instance, U.S. Pat. No. 5,885,381 to Mitose et al.

Clearly, self-expanding, nickel-titanium stents are useful and valuable to the medical field. But a distinct disadvantage with self-expanding nickel-titanium stents is the fact that they are not sufficiently radiopaque as compared to a comparable structure made from gold or tantalum. For example, radiopacity permits the cardiologist or physician to visualize the procedure involving the stent through use of fluoroscopes or similar radiological equipment. Good radiopacity is therefore a useful feature for self-expanding nickel-titanium stents to have.

Radiopacity can be improved by increasing the strut thickness of the nickel-titanium stent. But increasing strut thickness detrimentally affects the flexibility of the stent, which is a quality necessary for ease of delivery. Another complication is that radiopacity and radial force co-vary with strut thickness. Also, nickel-titanium is difficult to machine and thick struts exacerbate the problem.

Radiopacity can be improved through coating processes such as sputtering, plating, or co-drawing gold or similar heavy metals onto the stent. These processes, however, create complications such as material compatibility, galvanic corrosion, high manufacturing cost, coating adhesion or delamination, biocompatibility, loss of coating integrity following collapse and deployment of the stent, etc.

Radiopacity can also be improved by alloy addition. One specific approach is to alloy the nickel-titanium with tungsten yet not lose the engineering benefits of the superelastic material. What has been needed and heretofore unavailable in the prior art is a superelastic nickel-titanium stent that applies tungsten to increase radiopacity yet preserves the superelastic qualities of the nitinol.

SUMMARY OF THE INVENTION

The present invention is directed to a radiopaque stent for implantation in a body lumen and comprises a tubular-shaped body having a thin wall defining a strut pattern; wherein the body includes a nickel-titanium superelastic alloy, and the alloy further includes a ternary element including tungsten. As a result, the stent is highly radiopaque as compared to a similar structure made of medical grade stainless steel that is coated with a thin layer of gold.

Self-expanding nitinol stents are collapsed (that is, loaded) and then constrained within a delivery system. At the point of delivery, the stent is released (that is, unloaded) and allowed to return to its original diameter. The stent is designed to perform various mechanical functions within the lumen, all of which are based upon the lower unloading plateau stress. Therefore, it is crucial that the ternary element alloyed with the binary nickel-titanium does not diminish the superelastic characteristics of the nickel-titanium.

To achieve the sufficient degree of radiopacity yet maintaining the superelastic engineering properties of a binary nickel-titanium, preferably, the radiopaque stent of the present invention includes tungsten whose atomic percent is greater than or equal to 5 and less than or equal to 12. In various alternative embodiments, the atomic percent of the nickel is approximately 50.8, the atomic percent of the titanium is a maximum of approximately 40, and the atomic percent of the tungsten is approximately 10.

With such compositions, the stress-strain hysteresis curve of the present invention radiopaque nitinol alloy closely approximates the idealized stress-strain hysteresis curve of binary nickel-titanium. In other words, the present invention generally preserves the engineering qualities of the nitinol alloy yet improves upon its radiopacity.

The present invention further contemplates a method for providing a radiopaque nitinol stent. In a preferred embodiment, the method entails providing a tubular-shaped body having a thin wall, wherein the body includes a superelastic nickel-titanium alloy and the alloy further includes tungsten; and forming a strut pattern; wherein the stent is highly radiopaque. The step of providing a tubular-shaped body includes melting nickel with titanium and tungsten and cooling to form an ingot, hot rolling the alloy, cold forming the alloy into a cylinder, drilling the cylinder to form tubing, cold drawing the tubing, and annealing the tubing.

In a preferred embodiment, an austenite finish temperature ($A_f$) of the superelastic alloy in the stent is greater than or equal to zero and less than or equal to 30 degrees C. Also in the preferred embodiment, the Ni—Ti—W ingot prior to melting includes an austenite finish temperature ($A_f$) of greater than or equal to 0 degrees C. and less than or equal to 20 degrees C. The Ni—Ti—W tubing includes an austenite finish temperature ($A_f$) of greater than or equal to −15 degrees C. and less than or equal to 0 degrees C.

Other features and advantages of the present invention will become more apparent from the following detailed description of the invention when taken in conjunction with the accompanying exemplary drawings.

BRIEF DESCRIPTION OF THE DRAWINGS

FIG. 1 is a side elevational view, partially in section, depicting a stent mounted on a delivery catheter and expanded within a damaged vessel, pressing a damaged vessel lining against the vessel wall.

FIG. 2 is a side elevational view, partially in section, depicting an expanded stent within the vessel after withdrawal of the delivery catheter.

FIG. 3 is an idealized stress-strain hysteresis curve for a superelastic material.

DETAILED DESCRIPTION OF THE PREFERRED EMBODIMENTS

Figure 4:
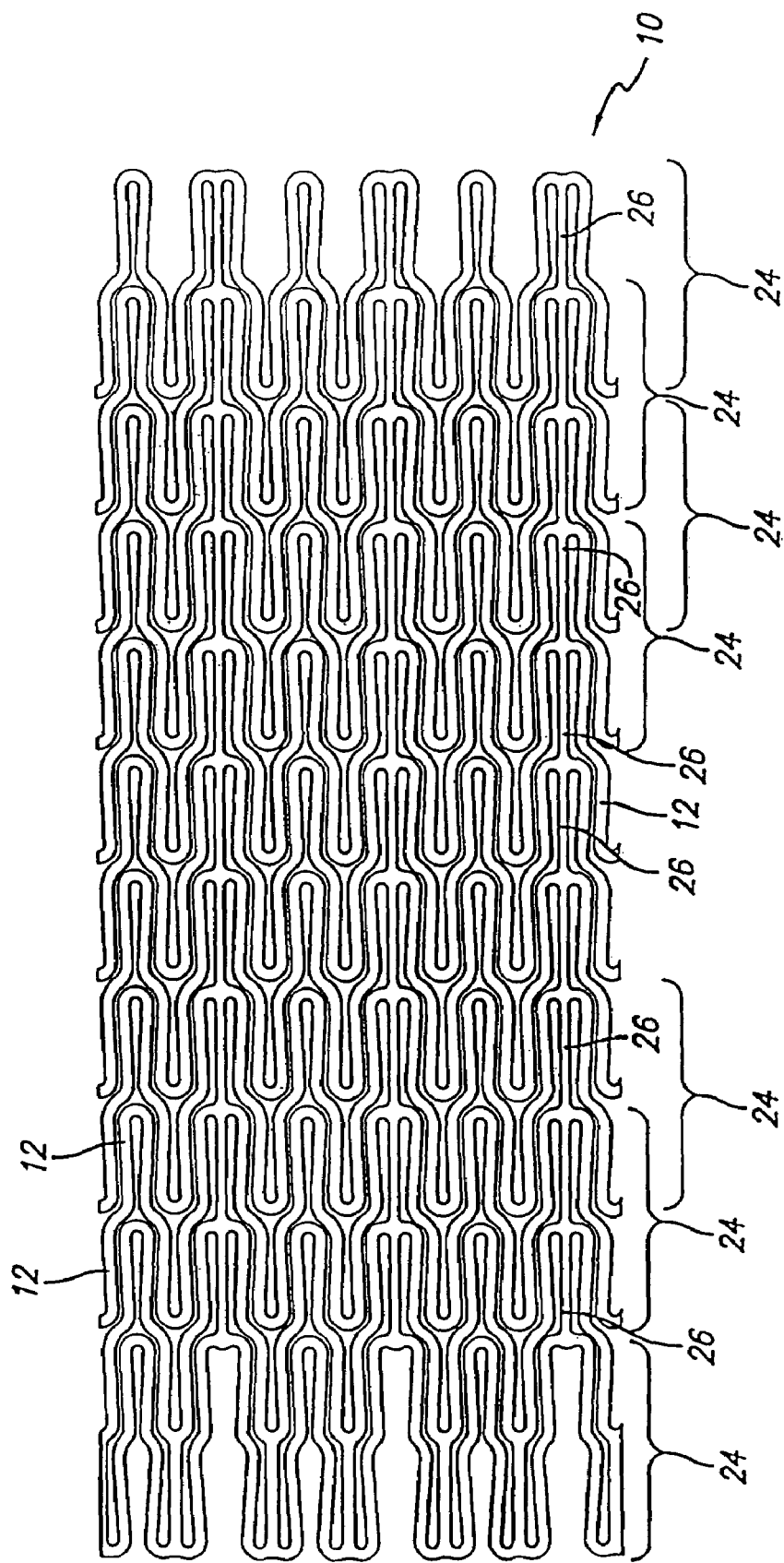
FIG. 4 is a plan view of the flattened strut pattern of an exemplary embodiment superelastic stent.

The present invention relates to stents made of radiopaque nitinol. The stents of the present invention can have virtually any configuration that is compatible with the body lumen in which they are implanted. The stent should preferably be configured so that there is a substantial amount of open area and preferably the open area to metal ratio is at least 80 percent. The stent should also be configured so that dissections or flaps in the body lumen wall are covered and tacked up by the stent.

Referring to FIGS. 1, 2, and 4, in a preferred embodiment, a stent 10 of the present invention is formed partially or completely of alloys such as nitinol (NiTi) which have superelastic (SE) characteristics. Stent 10 is somewhat similar to the stent disclosed in U.S. Pat. No. 5,569,295, "Expandable Stents and Method for Making Same," issued to Lam on Oct. 29, 1996, which patent is incorporated herein by reference. Some differences of the present invention stent from that disclosed in the '295 patent is that the present invention stent is preferably constructed of a superelastic material with the addition of a ternary element, and the strut pattern has changed. Of course, the configuration of the stent 10 is just one example of many stent configurations that are contemplated by the present invention.

Turning to FIG. 4, stent 10 preferably includes a plurality of radially expandable cylindrical elements 24 disposed generally coaxially and interconnected by members 26 disposed between adjacent cylindrical elements 24. The shapes of the struts 12 forming the pattern are designed so they can preferably be nested. This strut pattern is best seen from the flattened plan view of FIG. 4. The serpentine shaped struts 12 are nested such that the extended portions of the struts of one cylindrical element 24 intrude into a complementary space within the circumference of an adjacent cylindrical element. In this manner, the plurality of cylindrical elements 24 can be more tightly packed lengthwise.

As introduced above, an exemplary stent of the present invention includes a superelastic material. In a general sense, superelasticity implies that the material can undergo a large degree of reversible strain as compared to common steel. In a technical sense, the term "superelasticity" and sometimes "pseudoelasticity" refer to an isothermal transformation in nitinol. More specifically, it refers to stress inducing a martensitic phase from an austenitic phase. Alloys having superelastic properties generally have at least two phases: a martensitic phase, which has a relatively low tensile strength and which is stable at relatively low temperatures, and an austenitic phase, which has a relatively high tensile strength and which is stable at temperatures higher than the martensitic phase. Superelastic characteristics generally allow the metal stent to be deformed by collapsing and deforming the stent and creating stress which causes the NiTi to reversibly change to the martensitic phase. The stent is restrained in the deformed condition inside a delivery sheath typically to facilitate the insertion into a patient's body, with such deformation causing the isothermal phase transformation. Once within the body lumen, the restraint on the stent is removed, thereby reducing the stress thereon so that the superelastic stent returns to its original undeformed shape through isothermal transformation back to the austenitic phase. Under these conditions, the stent can be described as self-expanding.

Returning to FIG. 1, the graphic illustrates, in a partial cross-sectional view, the distal end of a rapid exchange stent delivery system that includes a guide wire 14, a delivery sheath 16, and an intravascular catheter 18. For the sake of clarity, the illustration of the delivery system in FIG. 1 has been simplified. It is just one example of a delivery system that may be used with the present invention. More details of a delivery system specifically for use with a self-expanding stent may be found in, for example, U.S. Pat. No. 6,077,295 to Limon et al., entitled "Self-Expanding Stent Delivery System," which is incorporated herein by reference. Other delivery systems such as over-the-wire may be used without departing from the scope of the instant invention.

FIG. 1 further shows an optional expandable balloon 20 inflated through an inflation lumen (not shown). The stent 10 is first crimped on to the deflated balloon 20, and the entire assembly is kept underneath the delivery sheath 16 until the moment the stent 10 is deployed. The stent 10 is self-expanding so that when the sheath 16 is withdrawn, the stent 10 expands to its larger, deployment diameter without assistance from the balloon 20. Nevertheless, some procedures specifically use the balloon 20 to further expand the stent 10 for improved seating in the artery wall 29.

FIG. 2 illustrates the self-expanding stent 10 in the expanded condition after the delivery system has been removed. If an external force is applied to the artery 28, the expanded stent 10 temporarily and at least partially collapses or deforms. As the stent 10 deforms, stress in the nickel-titanium alloy causes an isothermal phase transformation from the austenitic phase to the martensitic phase. When the external force is removed, the stress in stent 10 is likewise diminished so that the stent quickly transforms back from the martensitic phase to the austenitic phase. As this almost instantaneous, isothermal transformation occurs, the stent 10 returns to its fully expanded state and the artery remains open. When the superelastic stent 10 is implanted in an artery 28, its high resilience effectively maintains the patency of the artery while minimizing the risk of permanent arterial collapse at the implant site if the stent is temporarily deformed due to external forces. Furthermore, the resilience of the stent 10 supports the flap 30 to maintain patency of the artery.

Stent 10 is preferably formed from a superelastic material such as nickel-titanium and undergoes an isothermal transformation when stressed if in the austenitic phase. For most purposes, the transformation temperature for the stent 10 is preferably set low enough such that the nickel-titanium alloy is in the austenitic phase while at body temperature.

According to theory and practice, when stress is applied to a specimen of a metal such as nitinol exhibiting superelastic characteristics at a temperature at or above that which the transformation of the martensitic phase to the austenitic phase is complete, the specimen deforms elastically until it reaches a particular stress level where the alloy then undergoes a stress-induced phase transformation from the austenitic phase to the martensitic phase. As the phase transformation progresses, the alloy undergoes significant increases in strain with little or no corresponding increases in stress. The strain increases while the stress remains essentially constant until the transformation of the austenitic phase to the martensitic phase is complete (known as the "upper plateau"). Thereafter, further increase in stress is necessary to cause further deformation. The martensitic metal first yields elastically upon the application of additional stress and then plastically with permanent residual deformation.

If the load on the specimen is removed before any permanent deformation has occurred, the stress-induced martensite elastically recovers and transforms back to the austenitic phase. The reduction in stress first causes a decrease in strain. As stress reduction reaches the level at which the martensitic phase begins to transforms back into the austenitic phase, the stress level in the specimen remains essentially constant (but less than the constant stress level at which the austenitic crystalline structure transforms to the martensitic crystalline structure until the transformation back to the austenitic phase is complete); i.e., there is significant recovery in strain with only negligible corresponding stress reduction (known as the "lower plateau"). After the transformation back to austenite is complete, further strain reduction results in stress reduction. This ability to incur significant strain at relatively constant stress upon the application of a load and to recover from the deformation upon the removal of the load is commonly referred to as superelasticity and sometimes pseudoelasticity.

FIG. 3 illustrates an idealized stress-strain hysteresis curve for a superelastic, binary nickel-titanium alloy. The relationship is plotted on x-y axes, with the x axis representing strain and the y axis representing stress. For ease of illustration, the x-y axes are labeled on a scale typical for superelastic nitinol, with stress from 0 to 60 ksi and strain from 0 to 9 percent, respectively.

Looking at the plot in FIG. 3, the line from point A to point B represents the elastic deformation of the nickel-titanium alloy. After point B the strain or deformation is no longer proportional to the applied stress and it is in the region between point B and point C that the stress-induced transformation of the austenitic phase to the martensitic phase begins to occur. There also can be an intermediate phase, called the rhombohedral phase (or more commonly, the "R-Phase"), depending upon the composition and the thermomechanical history of the alloy.

At point C moving toward point D, the material enters a region of relatively constant stress with significant deformation or strain. This constant stress region is known as the loading plateau, since it represents the behavior of the material as it encounters continually increasing strain. It is in this plateau region C-D that the transformation from austenite to martensite occurs.

At point D the transformation to the martensitic phase due to the application of stress to the specimen is substantially complete. Beyond point D the martensitic phase begins to deform, elastically at first, but, beyond point E, the deformation is plastic or permanent.

When the stress applied to the superelastic metal is removed, the material behavior follows the curve from point E to point F. Within the E to F region, the martensite recovers its original shape, provided that there was no permanent deformation to the martensitic structure. At point F in the recovery process, the metal begins to transform from the stress-induced, metastable, martensitic phase back to the more stable austenitic phase.

In the region from point G to point H, which is also an essentially constant or plateau stress region, the phase transformation from martensite back to austenite takes place. This constant stress region G-H is known as the unloading plateau. The line from point I to the starting point A represents the elastic recovery of the metal to its original shape.

Binary nickel-titanium alloys that exhibit superelasticity have an unusual stress-strain relationship as just described and as plotted in the curve of FIG. 3. As emphasized above, the superelastic curve is characterized by regions of nearly constant stress upon loading, identified above as loading plateau stress C-D and unloading plateau stress G-H. Naturally, the loading plateau stress C-D always has a greater magnitude than the unloading plateau stress G-H. The loading plateau stress represents the period during which martensite is being stress-induced in favor of the original austenitic crystalline structure. As the load is removed, the stress-induced martensite transforms back into austenite along the unloading plateau stress part of the curve. The difference in stress between the stress at loading plateau C-D and unloading plateau G-H is the isothermal definition of the hysteresis in the system.

The present invention seeks to preserve the superelastic qualities of nickel-titanium alloys just described yet improve upon the material's radiopacity by addition of a ternary element. This is accomplished in one embodiment by forming a composition consisting essentially of about 30 to about 52 atomic percent titanium and the balance nickel and up to 10 atomic percent of one or more additional ternary alloying elements. The ternary alloy in the preferred embodiment is tungsten.

To achieve the sufficient degree of radiopacity yet maintaining the superelastic engineering qualities of a binary nickel-titanium, preferably, the radiopaque stent of the present invention includes tungsten whose atomic percent is greater than or equal to 5 and less than or equal to 12. In various alternative embodiments, the atomic percent of the nickel is approximately 50.8, the atomic percent of the titanium is a maximum of approximately 40, and the atomic percent of the tungsten is approximately 10.

A preferred method of fabricating the present invention superelastic, radiopaque metallic stent entails first fashioning nickel-titanium tubing. The tubing is made from vacuum induction melting nickel and titanium with tungsten according to the composition suggested above. The ingot is then remelted for consistency. The ingot is next hot rolled into bar stock, then straightened and sized, and cold formed into a cylinder. The cylinder is gun drilled to form the tubing. Instead of gun drilling, other methods of material removal known in the art may be used, including electric discharge machining (EDM), laser beam machining, and the like. Next, the tubing is cold or hot drawn and annealed repeatedly to achieve the finished dimensions.

Any of the foregoing preferred embodiment steps may be repeated, taken out of sequence, or omitted as necessary depending on desired results. From here on, the tubing follows conventional stent fabrication techniques such as laser cutting the strut pattern, heat setting, etc.

The following are additional guide posts for the nitinol processing to achieve a sufficiently radiopaque stent yet maintaining the superelastic stress-strain behavior of the alloy. In particular, empirical evidence suggests that the Ni—Ti—W ingot should preferably have the following austenite finish temperature: 0 degrees C.$\leq A_f \leq$20 degrees C. The Ni—Ti—W tubing should exhibit an austenite finish of: −15 degrees C.$\leq A_f \leq$0 degrees C. In an exemplary embodiment, the final laser cut Ni—Ti—W stent should exhibit an austenite finish temperature of: 0 degrees C.$\leq A_f \leq$30 degrees C. Of course, the $A_f$ of the finished laser cut stent can be set as needed by various heat treating processes known in the art.

It is understood that the austenite finish temperature ($A_f$) is defined to mean the temperature at which the material completely reverts to austenite. In technical terms, the $A_f$ (and other transformation temperatures $A_s$, $M_s$, $M_f$) as it applies to an ingot made of Ni—Ti—W, for example, is determined by a Differential Scanning Calorimeter (DSC) test, known in the art. The DSC test method to determine transformation temperatures for the ingot is guided by ASTM standard no. F 2004-00, entitled "Standard Test Method For Transformation Temperature Of Nickel-Titanium Alloys By Thermal Analysis."

The "active $A_f$" for the tubing and the finished stent is determined by a bend and free recovery test, also known in the art. In such a test, the tubing is cooled to under the $M_f$ temperature, deformed, and warmed up. While monitoring the increasing temperature, the point of final recovery of the deformation in the tubing approximates the $A_f$ of the material. The active $A_f$ testing technique is guided by a second ASTM standard entitled "Standard Test Method For Determination Of Transformation Temperature Of Nickel-Titanium Shape Memory Alloys By Bend And Free Recovery," or by equivalent test methods known in the art.

The present invention further provides a nitinol stent having improved radiopacity without resorting to increasing the wall thickness or strut thickness. Increasing wall or strut thicknesses detracts from the flexibility of the stent, which is detrimental to deliverability. Rather, the present invention superelastic nitinol stent has a thin wall/strut thickness and/or strut cross-sectional area akin to a conventional stainless steel stent, and has comparable radiopacity to a stainless steel stent with a thin coating of gold. The wall/strut thickness is defined by the difference between the inside diameter and the outside diameter of the tube. In an exemplary embodiment of the present invention, for an approximately 21 mm long stent with an expanded diameter of about 8 mm, the wall thickness is approximately 0.0045 inch. If the exemplary embodiment stent strut has a square shape cross-sectional area, its dimensions would be 0.0045 inch by 0.0045 inch with a cross-sectional area of approximately 0.000020 in$^2$.

Another aspect of nitinol aside from its superelasticity is shape memory. Sometimes, these two features of nitinol are loosely described as two sides of the same coin. The present invention can also be employed with respect to this "thermoelastic" physical attribute as described below.

The shape memory effect allows a nitinol structure to be deformed to facilitate its insertion into a body lumen or cavity, and then heated within the body so that the structure returns to its original, set shape. Nitinol alloys having shape memory effect generally have at least two phases: a martensitic phase, which has a relatively low tensile strength and which is stable at relatively low temperatures, and an austenitic phase, which has a relatively high tensile strength and which is stable at temperatures higher than the martensitic phase.

Shape memory effect is imparted to the alloy by heating the nickel-titanium metal to a temperature above which the transformation from the martensitic phase to the austenitic phase is complete; i.e., a temperature above which the austenitic phase is stable. The shape of the metal during this heat treatment is the shape "remembered." The heat-treated metal is cooled to a temperature at which the martensitic phase is stable, causing the austenitic phase to transform to the martensitic phase. The metal in the martensitic phase is then plastically deformed, e.g., to facilitate the entry thereof into a patient's body. Subsequent heating of the deformed martensitic phase to a temperature above the martensite to austenite transformation temperature causes the deformed martensitic phase to transform to the austenitic phase. During this phase transformation the metal reverts back to its original shape.

The recovery or transition temperature may be altered by making minor variations in the composition of the metal and in thermomechanical processing the material. In developing the correct composition, biological temperature compatibility must be determined in order to select the correct transition temperature. In other words, when the stent is heated, it must not be so hot that it is incompatible with the surrounding body tissue. Other shape memory materials may also be utilized, such as, but not limited to, irradiated memory polymers such as autocrosslinkable high density polyethylene (HDPEX). Shape memory alloys are known in the art and are discussed in, for example, "Shape Memory Alloys," *Scientific American*, Vol. 281, pp. 74-82 (November 1979), incorporated herein by reference.

Shape memory alloys undergo a transition between an austenitic phase and a martensitic phase at certain temperatures. When they are deformed while in the martensitic phase, they retain this deformation as long as they remain in the same phase, but revert to their original configuration when they are heated to a transition temperature, at which time they transform to their austenitic phase. The temperatures at which these transitions occur are affected by the nature of the alloy and the thermomechanical history of the material. Nickel-titanium-based alloys (NiTi), wherein the transition temperature is slightly lower than body temperature, are preferred for the present invention. It is desirable to have the transition temperature set at just below body temperature to insure a rapid transition from the martinsitic state to the austenitic state when the stent is implanted in a body lumen.

Turning again to FIGS. 1, 2, and 4, the present invention stent 10 is formed from a shape memory alloy, such as NiTi discussed above. After the stent 10 is inserted into an artery 28 or other vessel, the delivery sheath 16 is withdrawn exposing the stent 10 to the ambient environment. The stent 10 then immediately expands due to contact with the higher temperature within artery 28 as described for devices made from shape memory alloys. An optional expandable balloon 20 may be inflated by conventional means to further expand the stent 10 radially outward.

Again, if an external force is exerted on the artery, the stent 10 temporarily at least partially collapses. But the stent 10 then quickly regains its former expanded shape due to its shape memory qualities. Thus, a crush-resistant stent, having shape memory characteristics, is implanted in a vessel. It maintains the patency of a vessel while minimizing both the risk of permanent vessel collapse and the risk of dislodgment of the stent from the implant site if the stent is temporarily deformed due to external forces.

When the stent 10 is made in accordance with the present invention, it is also highly radiopaque. The same alloying processes described earlier are used here to add the ternary element to increase the radiopacity of the stent. Insofar as the martensitic to austenitic phase transformation is thermally driven, the deployment of the present invention stent can be explained in terms of the shape memory effect.

While the present invention has been illustrated and described herein in terms of a radiopaque nitinol stent, it is apparent to those skilled in the art that the present invention can be used in other instances. Other modifications and improvements may be made without departing from the scope of the present invention.

We claim:

1. Radiopaque tubing, comprising:
   a tubular-shaped body wherein the body includes a nickel-titanium superelastic alloy with a ternary element including tungsten, said alloy exhibiting a stress-strain curve that approximates the idealized stress-strain curve of binary nickel-titanium,
   wherein the body is radiopaque and the tubular-shaped body includes a strut pattern with struts no greater than 0.0046 inch in width.

2. The radiopaque tubing of claim 1, wherein the atomic percent of the tungsten greater than or equal to 5 and less than or equal to 12.

3. The radiopaque tubing of claim 1, wherein the atomic percent of the nickel is approximately 50.8, the atomic percent of the titanium is approximately 40, and the atomic percent of the tungsten is approximately 10.

4. The radiopaque tubing of claim 1, wherein the superelastic alloy includes a stress-induced martensite phase.

5. The radiopaque tubing of claim 1, wherein the atomic percent of the nickel is approximately 50.8, the atomic percent of the titanium is a maximum of approximately 40, and the atomic percent of the tungsten is approximately 10.

6. The radiopaque tubing of claim 1, wherein the superelastic alloy in the tubing with said strut pattern has an austenite finish temperature ($A_f$) of greater than or equal to zero and less than or equal to 30 degrees C.

7. The radiopaque tubing of claim 1, wherein the tubular-shaped body includes raw tubing having an austenite finish temperature ($A_f$) of greater than or equal to −15 degrees C. and less than or equal to 0 degrees C.

8. A superelastic, radiopaque metallic tubing for medical applications, comprising:
   a tubular-shaped body, wherein the body includes a superelastic nickel-titanium alloy and the alloy further includes tungsten, said alloy exhibiting a stress-strain curve that approximates the idealized stress-strain curve of binary nickel-titanium;
   wherein the tubular-shaped body is formed from a nickel-titanium-tungsten tubing that has undergone cold forming and heat treating and the tubular-shaped body includes a strut pattern with struts no greater than 0.0046 inch in width.

9. The superelastic, radiopaque metallic tubing of claim 8, wherein the atomic percent of the nickel is approximately 50.8, the atomic percent of the titanium is a maximum of approximately 40, and the atomic percent of the tungsten is approximately 10.

10. The superelastic, radiopaque metallic tubing of claim 8, wherein the atomic percent of the tungsten greater than or equal to 5 and less than or equal to 12.

11. The superelastic, radiopaque metallic tubing of claim 8, wherein the tubing includes a strut pattern having struts and each strut has a cross-sectional area of less than 0.000021 in$^2$.

12. The superelastic, radiopaque metallic tubing of claim 8, wherein the tubular-shaped body has been processed by melting nickel, titanium, and tungsten and cooling to the melt to form an alloy ingot, hot rolling the alloy ingot, cold and hot forming the alloy ingot into a cylinder, drilling the cylinder to form tubing, cold and hot drawing the tubing, and annealing the tubing.

13. Radiopaque tubing for medical applications, comprising, wherein said alloy exhibits a stress-strain curve that approximates the idealized stress-strain curve of binary nickel-titanium;
    a tubular body including a nickel-titanium alloy with at least a ternary element including tungsten, said alloy exhibiting a stress-strain curve that approximates the idealized stress-strain curve of binary nickel-titanium; and
    wherein the tubular body includes approximately 5 to 12 atomic percent tungsten such that the tubular body is radiopaque and the tubular-shaped body includes a strut pattern with struts no greater than 0.0046 inch in width.

14. The radiopaque tubing of claim 13, wherein the tubular body includes 10 atomic percent tungsten.

15. The radiopaque tubing of claim 13, wherein strut pattern provides a ratio of open area to metal of approximately 80 percent.

16. The radiopaque tubing of claim 13, wherein the nickel-titanium alloy includes transformation temperatures measured by a Differential Scanning Calorimeter (DSC) test.

17. The radiopaque tubing of claim 1, wherein the tubular-shaped body is formed from a nickel-titanium-tungsten tubing having an austenite finish temperature ranging from $-15°$ C. to $0°$ C.

18. The superelastic, radiopaque metallic tubing of claim 8, wherein the tubular-shaped body has an active austenite finish temperature $A_f$ defined by $-15°$ C. $\leq$ active $A_f \leq 0°$ C.

19. The radiopaque tubing of claim 13, wherein the tubular body has an austenite finish temperature ranging from $-15°$ C. to $0°$ C.

* * * * *